United States Patent [19]

Miller

[11] 4,084,595

[45] Apr. 18, 1978

[54] TRANSCUTANEOUS NERVE STIMULATOR

[75] Inventor: Curtis H. Miller, Burnsville, Minn.

[73] Assignee: Med General, Inc., Minneapolis, Minn.

[21] Appl. No.: 705,677

[22] Filed: Jul. 15, 1976

[51] Int. Cl.² .......................................... A61N 1/36
[52] U.S. Cl. ................................................ 128/422
[58] Field of Search ............... 128/421, 422, 423, 404, 128/409, 410, 418, 419, 1 C

[56]          References Cited
         U.S. PATENT DOCUMENTS

| | | | |
|---|---|---|---|
| 1,257,555 | 2/1918 | Vreeland | 128/410 X |
| 3,109,430 | 11/1963 | Tischler | 128/422 |
| 3,255,753 | 6/1966 | Wing | 128/421 |
| 3,464,416 | 9/1969 | Williams | 128/410 |
| 3,669,119 | 6/1972 | Symmes | 128/410 |
| 3,718,132 | 2/1973 | Holt et al. | 128/421 X |
| 3,911,930 | 10/1975 | Hagfors et al. | 128/421 |

Primary Examiner—William E. Kamm
Attorney, Agent, or Firm—Orrin M. Haugen

[57] ABSTRACT

Transcutaneous nerve stimulating apparatus wherein a portable, battery-operated variable pulse width, variable pulse rate oscillator is coupled through a variable amplitude current amplifying device to a set of electrodes adapted to be positioned upon the skin of a patient in proximity to a pain exhibiting area. The electrical signals or impulses are transmitted through the skin to the underlying nerves and serve to block the pain.

7 Claims, 2 Drawing Figures

TRANSCUTANEOUS NERVE STIMULATOR

BACKGROUND OF THE INVENTION

This invention relates generally to electromedical therapeutic apparatus and more specifically to an improved transcutaneous nerve stimulating apparatus for alleviating pain through the selective application of variable amplitude, variable pulse rate, variable pulse width electrical pulses to the skin in the area in which pain is experienced. It has been found that a proper application of such pulses serves to block the nerve responses and produce a beneficial effect.

In accordance with the teachings of the present invention, an integrated circuit timing network, energized by a rechargeable direct current battery is connected to an external resistor/capacitor charging circuit to form an astable oscillator whose pulse width and pulse rate are manually adjustable. The oscillator is coupled through a transistor current switching network and a step-up transformer to first and second pairs of electrodes. A current balancing network coupled between the output of the transformer and the electrodes allows the transformer output to be apportioned between the first and second electrode pairs. Another network, including a light emitting diode, is coupled to the integrated circuit timing network and is arranged to blink on and off when the rechargeable battery potential falls below a prearranged value, thus signaling the need for recharging.

SUMMARY OF THE INVENTION

It is accordingly an object of the present invention to provide an improved transcutaneous nerve stimulator which is portable, compact and convenient to operate.

Another object of this invention is to provide a portable transcutaneous nerve stimulator in which the amplitude, rate and pulse width of the applied electrical signals are selectively variable over a range of values by the patient.

Still another object of the invention is to provide an electronic pulse generator having a rechargable energy supply along with means for visually indicating the fact that the state of charge on the energy supply has deteriorated below a predetermined threshold value.

These and other objects and advantages of the invention will become apparent from a reading of the following detailed specification in conjunction with the accompanying drawings in which:

FIG. 1 is a pictorial drawing of the apparatus, showing the various controls; and FIG. 2 is a schematic diagram of the circuitry used in the preferred embodiment.

DESCRIPTION OF THE PREFERRED EMBODIMENT

Figure 1:
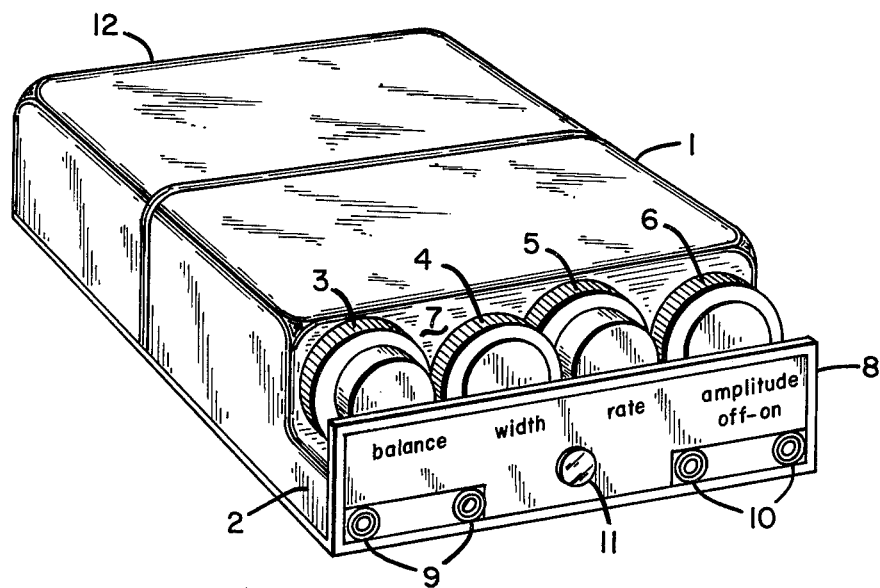

Referring first to FIG. 1, there is shown a perspective pictorial view of the transcutaneous nerve stimulator package arrangement. The package includes a substantially rectangular casing 1 which may be molded or otherwise formed from a suitable material such as plastic. The size of the package may, for example, be one inch thick by 3, inches wide by five inches long.

Located at the front end as viewed in FIG. 1, is a step-like projection or extension 2 which is integrally formed with the rest of the case 1. A plurality of thumb-wheel type control knobs 3, 4, 5 and 6 are mounted on shafts (not shown) which extend through apertures formed in the vertical riser 7. As will be explained more fully hereinbelow when the details of the electronic circuitry are described, these control knobs permit the user to control the rate, amplitude and pulse width of the electrical stimulating pulses produced by the transcutaneous nerve stimulator of this invention, as well as to control the balance of the electrical energy between first and second pairs of electrodes.

Affixed to the vertical front surface of the extension 2 is a display panel 8 having printed information thereon indicating the nature of the control obtained by the associated thumb-wheels 3, 4, 5 and 6. More specifically, thumb-wheel or knob 3 controls the balance of potential between first and second pairs of electrodes. Similarly, thumb-wheel 4 may be used to adjust the width of the stimulating pulses applied to the skin of the user via the electrodes (not shown). Thumb-wheels 5 and 6 respectively control the pulse rate and amplitude of the stimulating pulses. In addition, thumb-wheel 6 controls an "on-off" switch which is connected between the power for the unit and the electrical circuitry energized thereby.

First and second pairs of receptacles or jacks 9 and 10 are formed in the display panel 8 and extend into the casing 1 where they connect to operative elements of the electrical circuitry housed within the casing. Also illustrated in FIG. 1, on the face of the display panel 8 is an indicator 11 which, in the preferred embodiment, comprises a light-emitting diode (LED). As will be explained further, the indicator 11 serves to apprise the user of the charge condition of the energy source used to power the transcutaneous nerve stimulator of this invention.

The power source for the present invention is preferably a rechargeable DC battery pack (not shown). This pack is designed to be inserted and removed from its operative location within the housing 1 through an opening (not shown) formed in the rear end 12 of the housing. Because of its size and weight (approximately nine ounces) it can be seen that the device is readily portable and conveniently can be carried in a shirt pocket or, if desired, secured by a belt to a desired location on the body of the user.

Now that the general physical features of the device have been described, consideration will now be given to the electrical circuitry used in implementing the preferred embodiment.

Figure 2:
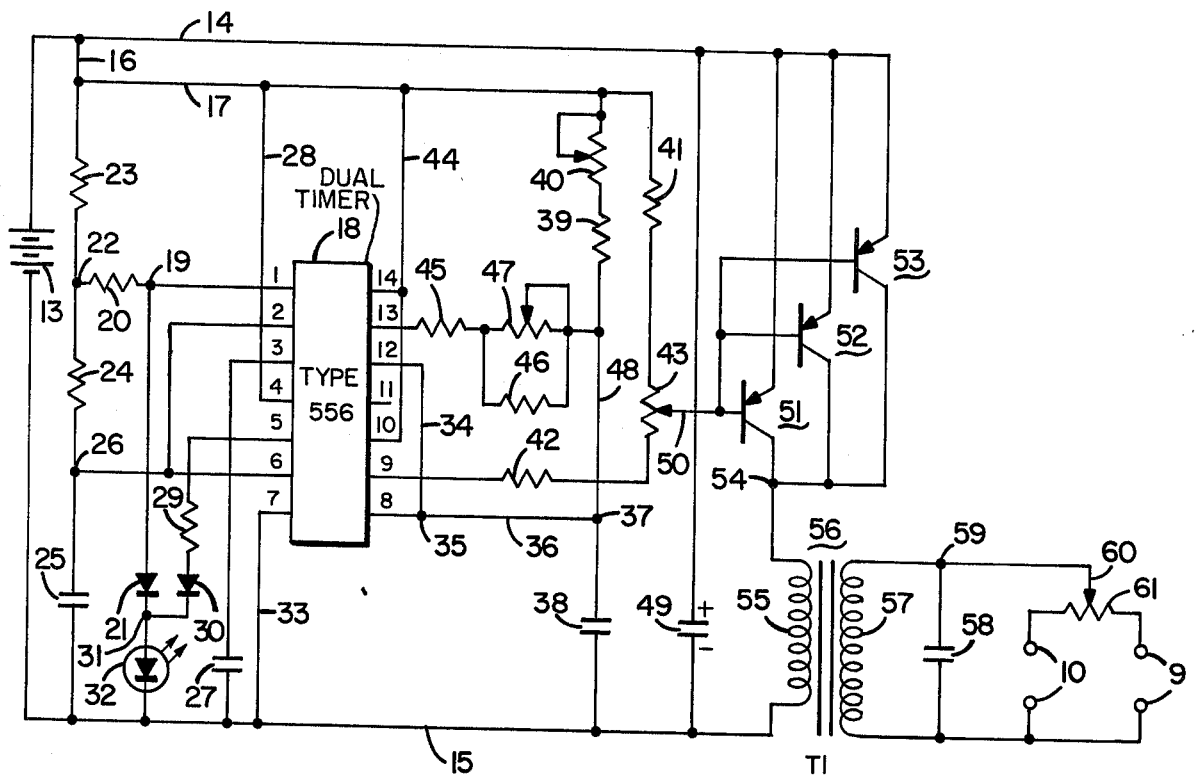

Referring to FIG. 2, there is shown a DC rechargeable battery 13 which is connected between the B+ bus 14 and a ground bus 15. The battery 13 may be such as to produce a potential difference of approximately five volts across its terminals when fully charged, but limitation to such a value is not intended. The B+ bus 14 is connected by a conductor 16 to the $V_{cc}$ bus 17.

Connected between the $V_{cc}$ bus 17 and the ground bus 15 is an integrated circuit chip 18. In the preferred embodiment of this invention, the chip 18 may be a Type 556 dual timer device such as manufactured by the Fairchild Semiconductor Division of the Fairchild Camera and Instrument Corporation. The chip 18 has 14 input/output pins which are respectively identified by the small numerals 1 through 14 located adjacent to the rectangular block representing the Type 556 chip. One desiring additional information concerning the construction and mode of operation of this integrated circuit chip is referred to the application notes provided by the manufacturers. For example, reference is made to the handbook entitled "Fairchild Linear Integrated Circuits" copyrighted in 1976 Lk and published by the Fairchild Camera and Instrument Company.

Pin 1 of the chip 18 is connected to a junction 19 between a resistor 20 and a semiconductor diode 21. The other terminal of resistor 20 is connected to a junction point 22 between the series combination of a resistor 23 and a resistor 24. Resistors 23 and 24 are serially connected with a capacitor 25 between the Vcc bus 17 and the ground bus 15. Pin 2 and Pin 6 of the chip 18 are connected together and to the junction point 26 formed between the resistor 24 and the capacitor 25. Pin 3 of IC chip 18 is coupled by means of a capacitor 27 to the ground bus 15. Pin 4 of chip 18 is connected by a conductor 28 to the $V_{cc}$ bus 17. Pin 5 of chip 18 is connected through a series combination of a resistor 29 and a semiconductor diode 30 to a junction point 31 to which the cathode of the diode 21 is connected. Connected between junction 31 and the ground bus 15 is a light-emitting diode 32. Pin 7 of chip 18 is connected directly to the ground bus 15 by a conductor 33.

Pin 8 and Pin 12 of the chip 18 are connected together by a jumper 34 at the junction point 35 which, in turn, is connected by a conductor 36 to a junction 37 formed between a capacitor 38 and a series combination of resistor 39 and a potentiometer 40. The end of potentiometer 40, not common to resistor 39, is connected to the Vcc bus 17. Coupled between the $V_{cc}$ bus 17 and Pin 9 of chip 18 is a series combination of first and second resistors 41 and 42 and a potentiometer 43. Pin 10 and Pin 14 of chip 18 are connected together and to the $V_{cc}$ bus 17 by way of a conductor 44. Pin 13 of chip 18 is coupled through a series resistor 45 and a parallel combination of a resistor 46 and a potentiometer 47 to a conductor 48 which is connected to the junction point 37.

A capacitor 49 is connected directly in parallel with the voltage source 13 between the B+ bus 14 and the ground bus 15. The wiper arm 50 of the potentiometer 43 is connected in common with the base electrodes of a plurality of transistors including PNP transistors 51, 52 and 53. The emitter electrodes of each of these transistors are tied directly to the B+ bus 14 and the collector electrodes thereof are connected in common to a junction point 54.

The primary winding 55 of a step-up transformer 56 is connected between the junction 54 and the ground bus 15. The step-up transformer 56 has a secondary winding 57 and connected in parallel with this secondary winding is a capacitor 58. The upper terminal 59 of secondary winding 57 is connected to the wiper arm 60 of a balancing potentiometer 61. Opposite ends of the potentiometer 61 are connected to the jack terminals 9 and 10 (FIG. 1).

This completes a description of the various electrical connections and components used in the implementation of the transcutaneous nerve stimulator of the present invention. Consideration will next be given to the mode of operation of this circuit.

Operation — FIG. 2

Before one can understand the operation of the overall circuit of FIG. 2, it is necessary to have some knowledge of the construction and mode of operation of the Type 556 integrated circuit chip 18 used therein. As is fully described in the aforereferences Fairchild Linear Integrated Circuit 1976 Handbook, the Type 556 IC chip is a dual timing circuit. More specifically, contained within the chip 18 are two identical timer units.

In the figure, Pins 1 through 7 provide the input, output and control connections to the first of the two timer circuits contained within chip 18, while Pins 8 through 14 provide the input, output and control functions for the second of the two timer units. In the preferred embodiment, the first of the two timer units is used to provide a visual indication that the battery has discharged to a point where recharging thereof is in order. More specifically, the first timer unit is connected so as to operate as an astable multivibrator whose output at Pin 5 is coupled through a resistor 29 and the diode 30 to the anode electrode of LED 32. As the multivibrator output oscillates between a predetermined positive voltage and ground, the junction 31 is alternately clamped at ground and allowed to assume a relatively high potential to thereby cause the LED 32 to turn on and off at a rate determined by the parameters of resistors 23, 24 and capacitor 25. In order for the timer unit to operate in an astable mode, the "reset" Pin 4 is tied to a high potential by way of conductor 28 and Pin 2 and Pin 6 are connected together and to the junction point 26 between the capacitor 25 and the resistor 24. It is this jumper connection between Pins 2 and 6 which causes the timer unit to trigger itself, i.e., free run as a multivibrator. When operating in the astable mode, the capacitor 25 charges and discharges between $\frac{1}{3} V_{cc}$ and $\frac{2}{3} V_{cc}$. The charging and discharging times of the capacitor 25 are independent of the magnitude of the supply voltage and therefore the frequency of oscillation is also substantially independent of supply voltage.

The point at which the LED 32 begins to blink can be expressed by the following inequality:

$$V_B < (V_{D32} + V_{D21}) \left( \frac{1 - \dfrac{R_{20}}{R_{23} + R_{20}}}{\dfrac{2}{3} - \dfrac{R_{20}}{R_{23} + R_{20}}} \right)$$

In the foregoing expression:
$V_{D32}$ is the voltage drop across the LED;
$V_{D21}$ is the drop across diode 21;
R20 and R23 and R25 are expressed in ohms; and
$V_B$ is the battery potential.

Thus, one can see that by judiciously selecting the values of the resistors 20 and 23, it is possible to predetermine the point at which the visual indication of a low battery potential will take place.

The second of the two timer units contained on the IC chip 18 along with the circuitry shown to the right of the chip 18 in FIG. 2 provides the nerve stimulating output pulses and the means for adjusting the amplitude, duration, frequency and balance thereof. Again, the connection between the trigger Pin 8 and the threshold Pin 12 of the chip 18 (conductor 34) causes the second timer unit on chip 18 to also operate in an astable mode. To prevent false resetting of the astable multivibrator, the reset Pin 10 of chip 18 is connected by means of conductor 44 to a relatively high potential. The output from the astable multivibrator appears at Pin 9. The potentiometer 40 in series with the resistor 39 controls the charging time of the capacitor 38. These three components determine the frequency at which output pulses will be produced. In the preferred embodiment, potentiometer 40, resistor 39 and capacitor 38 are of such a value that the frequency of the output signals can be made to vary between 10 and 100 Hz. The resistors 45 and 46 along with the potentiometer 47 in parallel with resistor 46, control the discharge time of the capacitor 38 and therefore by appropriately positioning the wiper arm of the potentiometer 47, the pulse width of the output from the timer unit can be controlled. In the preferred embodiment, the component values are chosen such that the pulse duration can be made to vary between 10 and 500 microseconds. For a given value of resistance in the potentiometer 47, the values of resistors 45 and 46 are chosen to give the desired end points for permissible pulse width.

As previously mentioned, the output signals from the second timer unit on the chip 18 appear at Pin 9 and swing between ground and a positive value determined by the ohmic values of resistors 40, 41 and 42 and the potentiometer 43. The output signals are used to control the conduction state of the parallel connected transistors 51, 52 and 53. The conduction level in these three transistors, in turn, may be controlled by the setting of the wiper arm 50 on the potentiometer 43. Hence, it is possible to control the amount of current flowing from the positive bus 14, through the parallel paths afforded by transistors 51, 52 and 53 and through the primary winding 55 of the step-up transformer 56. Thus, the setting of the wiper arm 50 determines the amplitude of the output pulses used to stimulate the body. The amplitude can be made to vary between 0 V and 35 V. In order to prevent thermal run-away in the parallel connected transistors 51, 52 and 53, it may be desirable to include resistors of identical ohmic values in series with the emitters of these transistors.

The changing current caused by the application of the timer output pulses to the parallel transistors 51, 52 and 53 causes a voltage to be induced across the secondary winding 57 of the transformer 56. The capacitor 58 connected in parallel with the secondary winding 57 serves to protect the transistors 51, 52 and 53 when an open circuit exists between the electrode jacks 9 and 10. The potentiometer 61 provides a means for balancing the distribution of load current as between the electrodes connected to jacks 10 and the electrodes connected to the jacks 9.

Thus, there is provided by this invention apparatus for producing variable amplitude, variable pulse width, variable frequency output signals to first and second electrode pairs. In addition, the invention includes circuitry for indicating when the level of charge on the rechargeable power pack has dropped below a given threshold.

Accordingly, it is seen that the present invention fully accomplishes its intended objects. While there has been disclosed and described in detail a preferred embodiment of the invention, that has been done by way of illustration, and not by way of limitation. It is realized that the transcutaneous nerve stimulator of the present invention can assume additional forms, and it is intended to include within the scope of the appended claims all modifications and variations naturally occurring to those skilled in the art.

I claim:

1. A transcutaneous nerve stimulator comprising in combination:
    (a) an astable multivibrator having a first resistance/capacitance timing circuit for controlling the frequency of the output pulses produced by said astable multivibrator and a second resistance/capacitance timing circuit for controlling the pulse width of said output pulses;
    (b) semiconductor current control means coupled by variable impedance means to receive said output pulses from said multivibrator;
    (c) a source of direct current voltage connected to said multivibrator, said first and second resistance/capacitance circuits and to said semiconductor current control means;
    (d) a transformer having a primary winding connected in series with said semiconductor current control means, the series combination being connected across said source of direct current voltage, and a secondary winding;
    (e) means coupling said secondary winding to first and second pairs of output terminals to which stimulator electrodes may be connected;
    (f) a third resistance/capacitance timing circuit connected across said source of direct current voltage;
    (g) a voltage divider connected to said source of direct current voltage for sensing the magnitude thereof;
    (h) indicating means connected to said voltage divider; and
    (i) a second astable multivibrator energized by said source of direct current voltage having an output terminal coupled to said indicating means and a trigger terminal connected to said third resistance/capacitance timing network, whereby said indicating means is continously energized when the magnitude of said direct current voltage is above a predetermined level and is alternately energized and deenergized when the magnitude of said direct current voltage drops said predetermined level, at a rate determined by said third resistance/capacitance timing circuit.

2. Apparatus as in claim 1 wherein the resistance in said first and second resistance/capacitor timing circuits is variable such that the frequency and pulse width of said output pulses produced by said multivibrator are manually adjustable.

3. Apparatus as in claim 1 wherein said variable impedance the means coupling the output pulses from said mutivibrator to said semiconductor current control means comprises a potentiometer for allowing manual control of the amplitude of the voltage induced across said secondary winding of said transformer.

4. Apparatus as in claim 3 wherein said means coupling said secondary winding to said first and second pairs of output terminals is a potentiometer having opposite ends thereof connected individually to a first output terminal of said first and second pairs of output terminals and its positionable tap connected to one end of said second winding, and wherein the second output terminal of said first and second pairs of output terminals are connected in common to the other end of said secondary winding such that the amount of current flowing to said first output terminals of said first and second pairs of output terminals can be balanced.

5. Apparatus as in claim 1 wherein said indicating means is a light-emitting diode.

6. Apparatus as in claim 1 wherein said astable multivibrators are semiconductor integrated circuits.

7. Apparatus as in claim 1 wherein said source of direct current voltage is a nickel-cadmium rechargeable battery.

* * * * *

UNITED STATES PATENT OFFICE
CERTIFICATE OF CORRECTION

PATENT NO. : 4,084,595
DATED : April 18, 1978
INVENTOR(S) : Curtis H. Miller

It is certified that error appears in the above-identified patent and that said Letters Patent are hereby corrected as shown below:

Column 3, line 1, delete the letters "Lk" after -- 1976 --.

Column 4, line 45, delete the phrase "and R25".

Column 6, line 43, delete the word "the" (first occurrence).

Signed and Sealed this

Fifteenth Day of August 1978

[SEAL]

Attest:

RUTH C. MASON
Attesting Officer

DONALD W. BANNER
Commissioner of Patents and Trademarks